(12) United States Patent
Peabody, III

(10) Patent No.: US 10,765,692 B2
(45) Date of Patent: Sep. 8, 2020

(54) MARIBAVIR ISOMERS, COMPOSITIONS, METHODS OF MAKING AND METHODS OF USING

(71) Applicant: Shire ViroPharma Incorporated, Lexington, MA (US)

(72) Inventor: John D. Peabody, III, West Chester, PA (US)

(73) Assignee: Shire Viropharma Incorporated, Lexington, MA (US)

( * ) Notice: Subject to any disclaimer, the term of this patent is extended or adjusted under 35 U.S.C. 154(b) by 0 days.

(21) Appl. No.: 16/663,743

(22) Filed: Oct. 25, 2019

(65) Prior Publication Data

US 2020/0054658 A1 Feb. 20, 2020

Related U.S. Application Data

(60) Division of application No. 15/291,639, filed on Oct. 12, 2016, now Pat. No. 10,485,813, which is a division of application No. 15/055,043, filed on Feb. 26, 2016, now abandoned, which is a continuation of application No. 14/595,548, filed on Jan. 13, 2015, now abandoned, which is a continuation of application No. 13/282,501, filed on Oct. 27, 2011, now Pat. No. 8,940,707.

(60) Provisional application No. 61/407,637, filed on Oct. 28, 2010.

(51) Int. Cl.
| | |
|---|---|
| *A61K 31/7056* | (2006.01) |
| *A61K 45/06* | (2006.01) |
| *G09B 19/00* | (2006.01) |
| *G01N 33/94* | (2006.01) |

(52) U.S. Cl.
CPC .......... *A61K 31/7056* (2013.01); *A61K 45/06* (2013.01); *G01N 33/94* (2013.01); *G09B 19/00* (2013.01); *G01N 2430/00* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 6,037,153 A | 3/2000 | Izumori et al. | |
| 6,077,832 A | 6/2000 | Chamberlain et al. | |
| 6,469,160 B1 | 10/2002 | Glover et al. | |
| 6,482,939 B1 | 11/2002 | Hodgson et al. | |
| 8,541,391 B2 | 9/2013 | Amparo et al. | |
| 8,546,344 B2 | 10/2013 | Coquerel et al. | |
| 8,940,707 B2 | 1/2015 | Peabody | |
| 10,485,813 B2* | 11/2019 | Peabody, III | G01N 33/94 |
| 2015/0126470 A1 | 5/2015 | Peabody, III | |
| 2016/0175338 A1 | 6/2016 | Peabody, III | |
| 2016/0304549 A1 | 10/2016 | Coquerel et al. | |
| 2017/0027974 A1 | 2/2017 | Peabody, III | |

OTHER PUBLICATIONS

Ahmed, Z., Bacterial L-Ribose and L-arabinose Isomerase: Production, Isolation, Immbolization and Characterization, Bangladesh J. Sci. Ind. Res., 35:89-104 (2000).
Ahmed, Z., Biochemical Preparation of L-Ribose and L-Arabinose from Ribitol: A New Approach, Journal of Bioscience and Bioengineering, 88(4):444-448 (1999).
Banker, G.S. et al., Modern Pharmaceutics, 3ed., Marcel Dekker, New York, 596 (1996).
Beigelman, L., Epimerization During the Acetolysis of 3-O-Acetyl-5-O-Benzoyl-1,2-O-Isopropylidene-3-C-Methyl-α-D-Ribofuranose. Synthesis of 3'-C-Methylnucleosides with the β-D-ribo- and α-D-arabino Configurations, Carbohydrate Research, 181:77-88 (1988).
Benner, S., Understanding Nucleic Acids Using Synthetic Chemistry, Acc. Chem. Res., 37:784-797 (2004).
Kelley, J., Furanose-Pyranose Isomerization of Reduces Pyrimidine and Cyclic Urea Ribosides, J. Med. Chem., 29:2351-2358 (1986).
Okano, K., Synthesis and pharmaceutical application of L-ribose, Tetrahedron, 65:1937-1949 (2009).
Samuel, J., Mechanistic aspects of enzymatic carbohydrate epimerization, Nat. Prod. Rep., 19:261-277 (2002).
ViroPharma Press Release dated Feb. 9, 2009.
ViroPharma Press Release dated Mar. 29, 2006.
Wolff, M.E., Burger's Medicinal Chemistry, 5ed, Part I, John Wiley & Sons, 975-977 (1995).

* cited by examiner

*Primary Examiner* — Traviss C McIntosh, III
(74) *Attorney, Agent, or Firm* — Choate, Hall & Stewart LLP; John P. Rearick; Cristin E. Juda

(57) ABSTRACT

The invention relates to novel compositions and methods of using maribavir which enhance its effectiveness in medical therapy, as well as to maribavir isomers and methods of use thereof for counteracting the potentially adverse effects of maribavir isomerization in vivo in the event it occurs.

9 Claims, 4 Drawing Sheets

Maribavir

MFI-01

MFI-02

MFI-03

MFI-05

MFI-06

MFI-04

MFI-07

MARIBAVIR ISOMERS, COMPOSITIONS, METHODS OF MAKING AND METHODS OF USING

CROSS-REFERENCE TO RELATED APPLICATIONS

The present application is a divisional of U.S. patent application Ser. No. 15/291,639, filed Oct. 12, 2016, which is a divisional of U.S. patent application Ser. No. 15/055,043, filed Feb. 26, 2016, which is a continuation of U.S. patent application Ser. No. 14/595,548, filed Jan. 13, 2015, which is a continuation of U.S. Pat. No. 8,940,707, filed Oct. 27, 2011, which claims the benefit of U.S. Provisional Patent Application No. 61/407,637, filed Oct. 28, 2010, the entire disclosure of which is incorporated by reference herein.

BACKGROUND OF THE INVENTION

The present invention relates to compositions and methods for enhancing the therapeutic efficacy of the compound 5,6-dichloro-2-(isopropylamino)-1-(β-L-ribofuranosyl)-1H-benzimidazole (also known as 1263W94 and maribavir), as well as to maribavir isomers and a method of making such isomers.

5,6-dichloro-2-(isopropylamino)-1-(β-L-ribofuranosyl)-1H-benzimidazole is a benzimidazole derivative useful in medical therapy. U.S. Pat. No. 6,077,832 discloses 5,6-dichloro-2-(isopropylamino)-1-(β-L-ribofuranosyl)-1H-benzimidazole and its use for the treatment or prophylaxis of viral infections such as those caused by herpes viruses. The compound as disclosed in U.S. Pat. No. 6,077,832 is an amorphous, non-crystalline material.

The structure of 5,6-dichloro-2-(isopropylamino)-1-(β-L-ribofuranosyl)-1H-benzimidazole is:

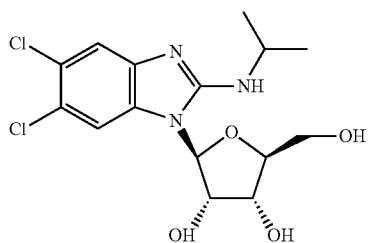

(I)

The preparation of certain unique crystalline forms and solvate forms of maribavir, as well as pharmaceutical formulations thereof and their use in therapy are described in U.S. Pat. Nos. 6,469,160 and 6,482,939.

The present invention has arisen out of the unexpected discovery that maribavir may isomerize under in vivo conditions to one or more configurational stereoisomers or constitutional isomers. The maribavir compound contains 4 (four) chiral carbon centers in the ribofuranosyl moiety and therefore maribavir is just one of 16 (sixteen) potential stereoisomers that may be formed under various in vivo conditions.

Under in vivo conditions, maribavir can isomerize to other compounds that may (or may not) have the same or similar chemical, physical and biological properties. The in vivo isomerization of maribavir results in conversion of maribavir to other isomers that have the same molecular formula but a different molecular structure. The different molecular structures can be grouped into isomers that have different connectivity of the constituent atoms (constitutional isomers) or grouped into isomers that have the same "connectivity" but differ in the way the atoms and groups of atoms are oriented in space (configurational stereoisomers). Such molecular conversion in vivo is believed to result in the dilution of the effective maribavir concentration in the host that was treated with maribavir. The in vivo isomerization transforms and distributes dosed maribavir material into other molecular entities that do not necessarily have the same or similar biological activity. If the isomerization results in the formation of isomers that have a lower degree of corresponding biological activity relative to the activity of maribavir, then the isomerization will decrease the effective biological activity of maribavir dose administered to a host.

A recent maribavir Phase 3 clinical trial conducted by ViroPharma Incorporated (the 300 Study) that evaluated maribavir for cytomegalovirus (CMV) prophylaxis in allogeneic stem cell, or bone marrow, transplant (SCT) patients did not achieve its primary endpoint. In the primary analysis, there was no statistically significant difference between maribavir and placebo in reducing the rate of CMV disease. In addition, the study failed to meet its key secondary endpoints (ViroPharma Press Release dated Feb. 9, 2009). The 300 Study result appeared at first blush to be inconsistent with an earlier proof-of-concept (POC) maribavir Phase 2 clinical trial (the 200 Study) wherein ViroPharma reported positive preliminary results that showed that maribavir inhibited CMV reactivation in SCT patients. The data from this study demonstrate that prophylaxis with maribavir displays strong antiviral activity, as measured by significant reduction in the rate of reactivation of CMV in recipients of allogeneic stem cell (bone marrow) transplants, and that administration of maribavir for up to 12 weeks has a favorable tolerability profile in this very sick patient population (ViroPharma Press Release date Mar. 29, 2006).

However, the 300 Study result can be explained in terms of the instant maribavir isomerization theory/discovery. An unrecognized key difference between the 200 Study and the 300 Study was that the former provided for a fasted dosing protocol of maribavir, whereas the latter allowed the dosing protocol to be either under fasted or fed conditions (at the discretion of the clinician). The nature of the patient population in the 300 Study suggests that probably very few patients were dosed under the strict fasted dosing protocol that was previously used in the 200 Study. The change in dosing protocol in the 300 Study changed not only the in vivo dosing conditions for maribavir, but also the nature and/or degree of isomerization of maribavir that occurs in vivo, so that more maribavir was isomerized to other less effective compounds, thereby reducing the effective bioavailable concentration of maribavir drug below levels necessary to adequately prevent CMV infection and/or CMV re-activation in the host.

The degree and nature of the isomerization of maribavir depends on the particular in vivo conditions to which the drug is exposed, which are variable. The potential mechanisms for isomerizing maribavir in vivo are by chemical isomerization (acid, base and/or metal catalyzed isomerization), microbially-mediated isomerization, and/or host metabolism induced isomerization. See, for example, Okano, Kazuya, Tetrahedron, 65: 1937-1949 (2009); Kelly, James A. et al., J. Med. Chem., 29: 2351-2358 (1986); and Ahmed, Zakaria et al., Bangladesh J. Sci. Ind. Res., 25(1-4): 90-104 (2000).

Thus, maribavir should be formulated, administered, packaged and promoted in ways that will prevent or at least reduce the unwanted occurrence of maribavir isomerization in vivo, thereby enhancing the drug's bioavailability and efficacy, and/or counteract the potential adverse effect(s) of maribavir isomerization in vivo, if it occurs.

SUMMARY OF THE INVENTION

The invention generally relates to the unexpected discovery that maribavir may isomerize under in vivo conditions to one or more configurational stereoisomers and/or constitutional isomers. Aspect of the invention is illustrated below.

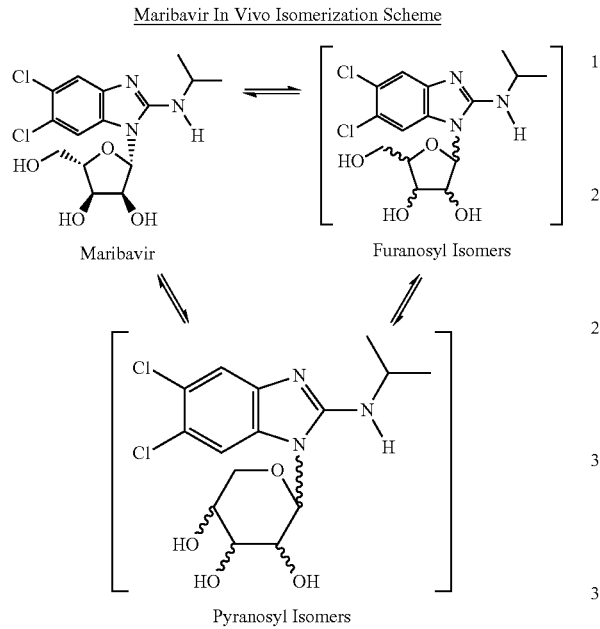

Maribavir In Vivo Isomerization Scheme

The practical applications of the instant discovery and related inventions are as follows:

(1) The invention includes methods of making maribavir isomers under in vivo conditions (method of administering maribavir as a prodrug to make other maribavir isomers).

(2) The invention includes methods dosing maribavir so as to mitigate the impact of in vivo maribavir isomerization (such as dosing under fasted conditions, or increasing the dose of maribavir).

(3) The invention includes maribavir formulations that effectively mitigate the adverse effects of in vivo maribavir isomerization (quick release formulations, delayed/controlled release formulations, combination with antacids, intravenous (IV) formulations, combination formulations with antibiotics to prevent microbial isomerization).

(4) The invention includes methods of using one or more maribavir isomers to prevent or treat disease in host (as antivirals, for example for treating/preventing CMV, EBV, HCV).

(5) The invention includes methods of using one or more maribavir isomers as reference standards in analytical methods for monitoring the blood plasma concentrations of maribavir and related isomers.

(6) The invention includes methods of monitoring maribavir and maribavir isomers, and using the information to adjust treatment protocols (increase/decrease dose, change dosing regimen fed/fasted, discontinue maribavir therapy, start other therapy). The analytical methods for monitoring in vivo maribavir concentrations must be able discriminate between maribavir and maribavir isomers (for example chiral chromatography, and in particular LC-MS-MS using a chiral sorbent material in the LC column).

(7) The invention includes a method of more safely and effectively using maribavir to treat or prevent disease in humans by including information and guidance in the product label and/or promotional materials to inform the public as to how to use the maribavir product so as to avoid or to mitigate the adverse impact of in vivo maribavir isomerization, and thus optimize therapeutic efficacy and safety.

(8) The invention includes the corresponding inventions related to the maribavir isomers that are pyranosyl constitutional isomers of maribavir.

The present invention also relates to a package or kit comprising therapeutically effective dosage forms of maribavir, prescribing information and a container for the dosage form. The prescribing information includes advice to a patient receiving maribavir therapy regarding the administration of maribavir without food to improve bioavailability.

DETAILED DESCRIPTION OF THE INVENTION

The following table contains list of useful dosing protocols that may be used to improve the efficacy and safety for treating a patient with maribavir.

| Maribavir dosing Protocol | Dosing amount | Fasting conditions (before/ after dosing) | Route of administration and dosage form. |
| --- | --- | --- | --- |
| 01 | 3200 mg/2 × day | None | Oral-tablet-immediate release |
| 02 | 3200 mg/2 × day | None | IV |
| 03 | 1600 mg/2 × day | None | Oral-tablet-w/ antacids |
| 04 | 1600 mg/1 × day | None | Oral-tablet-w/antibiotics |
| 05 | 800 mg/3 × day | None | Oral-tablet-delayed release |
| 06 | 800 mg/2 × day | None | Oral-tablet-immediate release |
| 07 | 800 mg/1 × day | None | IV |
| 08 | 400 mg/4 × day | None | Oral-tablet-w/ antacids |
| 09 | 400 mg/3 × day | None | Oral-tablet-w/antibiotics |
| 10 | 400 mg/2 × day | None | Oral-tablet-delayed release |
| 11 | 400 mg/1 × day | None | Oral-tablet-immediate release |
| 12 | 3200 mg/2 × day | 12 hrs/3 hrs | IV |
| 13 | 3200 mg/2 × day | 12 hrs/3 hrs | Oral-tablet-w/ antacids |
| 14 | 1600 mg/2 × day | 12 hrs/3 hrs | Oral-tablet-w/antibiotics |
| 15 | 1600 mg/1 × day | 12 hrs/3 hrs | Oral-tablet-delayed release |
| 16 | 800 mg/3 × day | 12 hrs/3 hrs | Oral-tablet-immediate release |
| 17 | 800 mg/2 × day | 12 hrs/3 hrs | IV |
| 18 | 800 mg/1 × day | 12 hrs/3 hrs | Oral-tablet-w/ antacids |
| 19 | 400 mg/4 × day | 12 hrs/3 hrs | Oral-tablet-w/antibiotics |
| 20 | 400 mg/3 × day | 12 hrs/3 hrs | Oral-tablet-delayed release |
| 21 | 400 mg/2 × day | 12 hrs/3 hrs | Oral-tablet-immediate release |
| 22 | 400 mg/1 × day | 12 hrs/3 hrs | Oral-tablet-immediate release |
| 23 | 3200 mg/2 × day | 6 hrs/2 hrs | Oral-tablet-immediate release |
| 24 | 3200 mg/2 × day | 6 hrs/2 hrs | IV |
| 25 | 1600 mg/2 × day | 6 hrs/2 hrs | Oral-tablet-w/ antacids |
| 26 | 1600 mg/1 × day | 6 hrs/2 hrs | Oral-tablet-w/antibiotics |
| 27 | 800 mg/3 × day | 6 hrs/2 hrs | Oral-tablet-delayed release |
| 28 | 800 mg/2 × day | 6 hrs/2 hrs | Oral-tablet-immediate release |

-continued

| Maribavir dosing Protocol | Dosing amount | Fasting conditions (before/ after dosing) | Route of administration and dosage form. |
|---|---|---|---|
| 29 | 800 mg/1 × day | 6 hrs/2 hrs | IV |
| 30 | 400 mg/4 × day | 6 hrs/2 hrs | Oral-tablet-w/ antacids |
| 31 | 400 mg/3 × day | 6 hrs/2 hrs | Oral-tablet-w/antibiotics |
| 32 | 400 mg/2 × day | 6 hrs/2 hrs | Oral-tablet-delayed release |
| 33 | 400 mg/1 × day | 6 hrs/2 hrs | Oral-tablet-immediate release |
| 34 | 3200 mg/2 × day | 3 hrs/1 hr | IV |
| 35 | 3200 mg/2 × day | 3 hrs/1 hr | Oral-tablet-w/ antacids |
| 36 | 1600 mg/2 × day | 3 hrs/1 hr | Oral-tablet-w/antibiotics |
| 37 | 1600 mg/1 × day | 3 hrs/1 hr | Oral-tablet-delayed release |
| 38 | 800 mg/3 × day | 3 hrs/1 hr | Oral-tablet-immediate release |
| 39 | 800 mg/2 × day | 3 hrs/1 hr | IV |
| 40 | 800 mg/1 × day | 3 hrs/1 hr | Oral-tablet-w/ antacids |
| 41 | 400 mg/4 × day | 3 hrs/1 hr | Oral-tablet-w/antibiotics |
| 42 | 400 mg/3 × day | 3 hrs/1 hr | Oral-tablet-delayed release |
| 43 | 400 mg/2 × day | 3 hrs/1 hr | Oral-tablet-immediate release |
| 44 | 400 mg/1 × day | 3 hrs/1 hr | Oral-tablet-immediate release |

In carrying out the method of the invention, it is preferably to determine the presence and/or concentration of maribavir isomers, especially isomers of diminished therapeutic efficacy in patient blood plasma samples as part of the method.

As used herein, the terms "fasted conditions", "fasting conditions" and "without food" are defined to mean, in general, the condition of not having consumed food during the period between from at least about 3 to 12 hours prior to the administration of maribavir to at least about 1 to 3 hours after the administration of maribavir. Other narrower "fasted conditions" are also contemplated herein and described below.

The term "with food" is defined to mean, in general, the condition of having consumed food prior to, during and/or after the administration of maribavir that is consistent with the relevant intended definition of "fasted conditions" (which may be narrow or broad depending on the circumstances). Preferably, the food is a solid food sufficient bulk and fat content that it is not rapidly dissolved and absorbed in the stomach. More preferably, the food is a meal, such as breakfast, lunch or dinner.

The term "isomers" means compounds that have the same molecular formula but a different molecular structure.

The term "constitutional isomers" is defined to mean isomers that have the same molecular formula but a different molecular structure wherein the molecular structures of the isomers have different connectivity of the constituent atoms.

The term "configurational stereoisomers" is defined to mean isomers that have the same "connectivity" but differ in the molecular structure in the way the atoms and groups of atoms are oriented in space.

The term "immediate release" is defined to mean release of drug from drug formulation by dissolution is less than 60 minutes or is otherwise release from the drug formulation in less than 60 minutes.

The term "IV" is defined to mean intravenous.

The chemical structure of maribavir and some maribavir isomers are shown below. The instant invention contemplates novel formulations, dosage levels and methods of use of maribavir, the maribavir isomers MFI-01 to MFI-015 (configurational stereoisomers), as well as the maribavir isomers MPI-01 to MPI-016 (constitutional isomers). The invention also contemplates the corresponding acyclic constitutional isomers wherein the sugar moiety is an open chain and attached to the benzimidazole.

Figure 1:
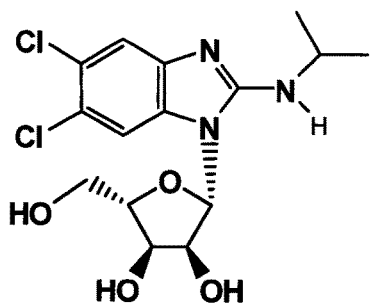
FIG. 1 shows chemical structures of maribavir and maribavir configurational stereoisomers that have the same configuration at the furanoysl anomer carbon.
Figure 1:
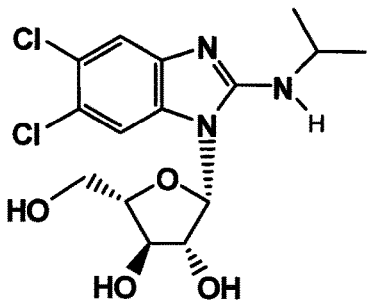
Figure 1:
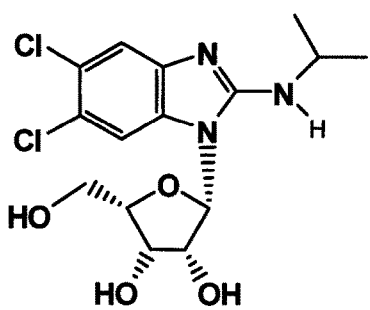
Figure 1:
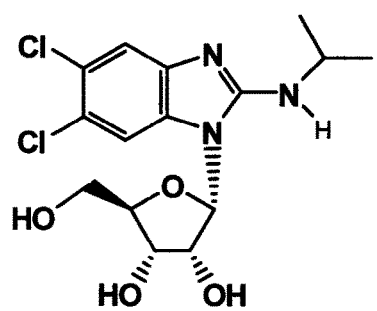
Figure 1:
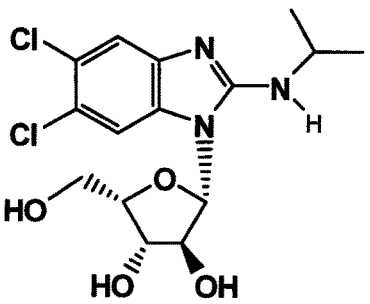
Figure 1:
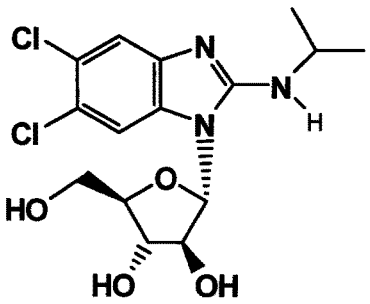
Figure 1:
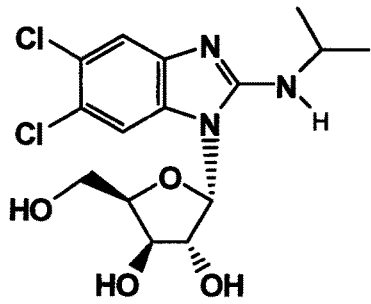
Figure 1:
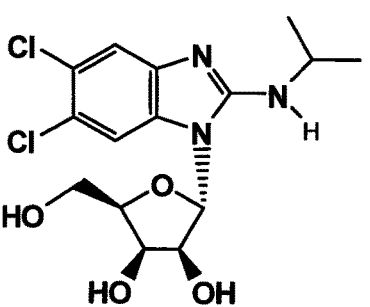
Figure 2:
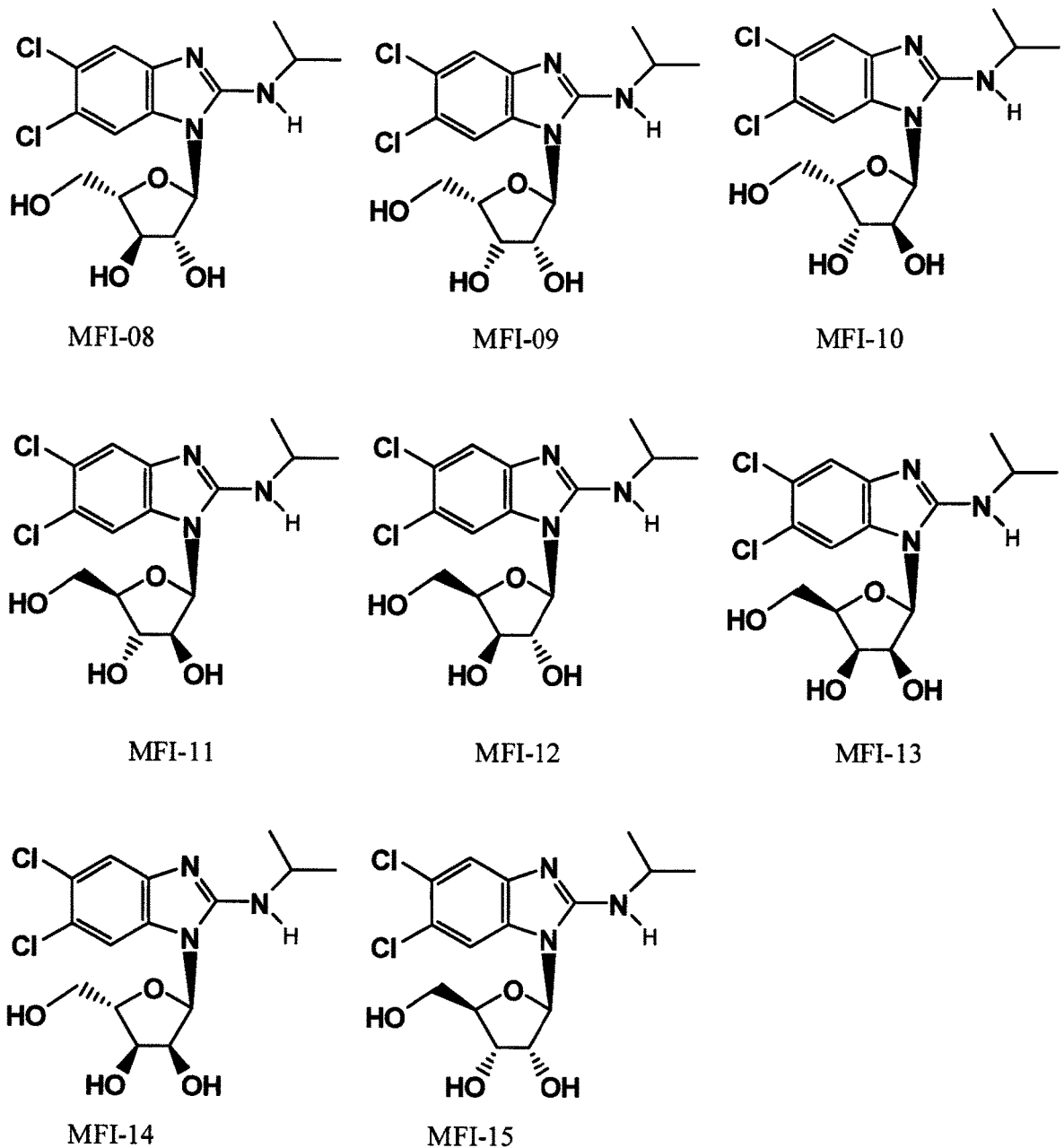
FIG. 2 shows chemical structures of maribavir configurational stereoisomers that have the opposite configuration at the furanosyl anomer carbon.
Figure 3:
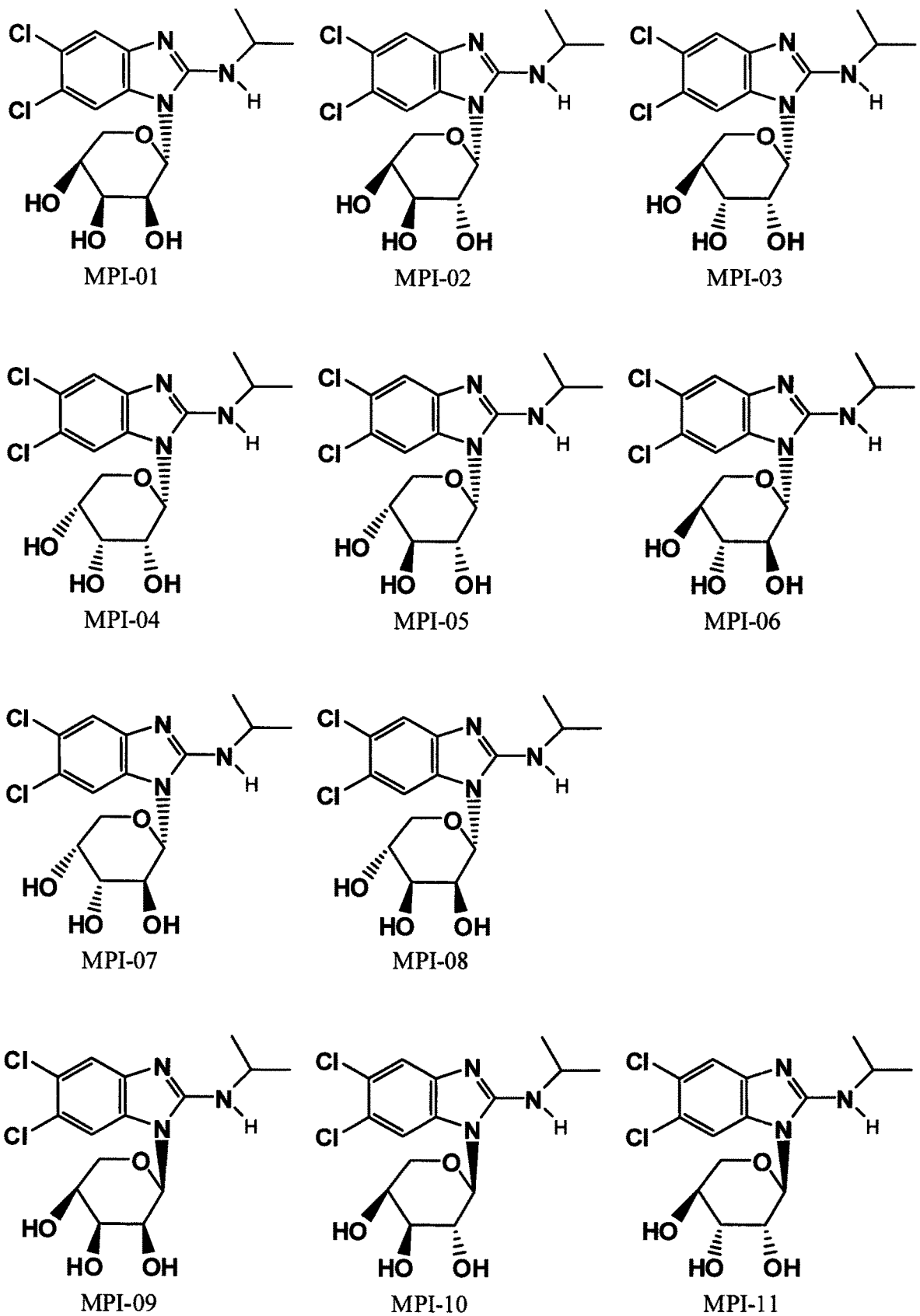
FIG. 3 shows chemical structures of maribavir "pyranosyl" constitutional isomers)
Figure 3:
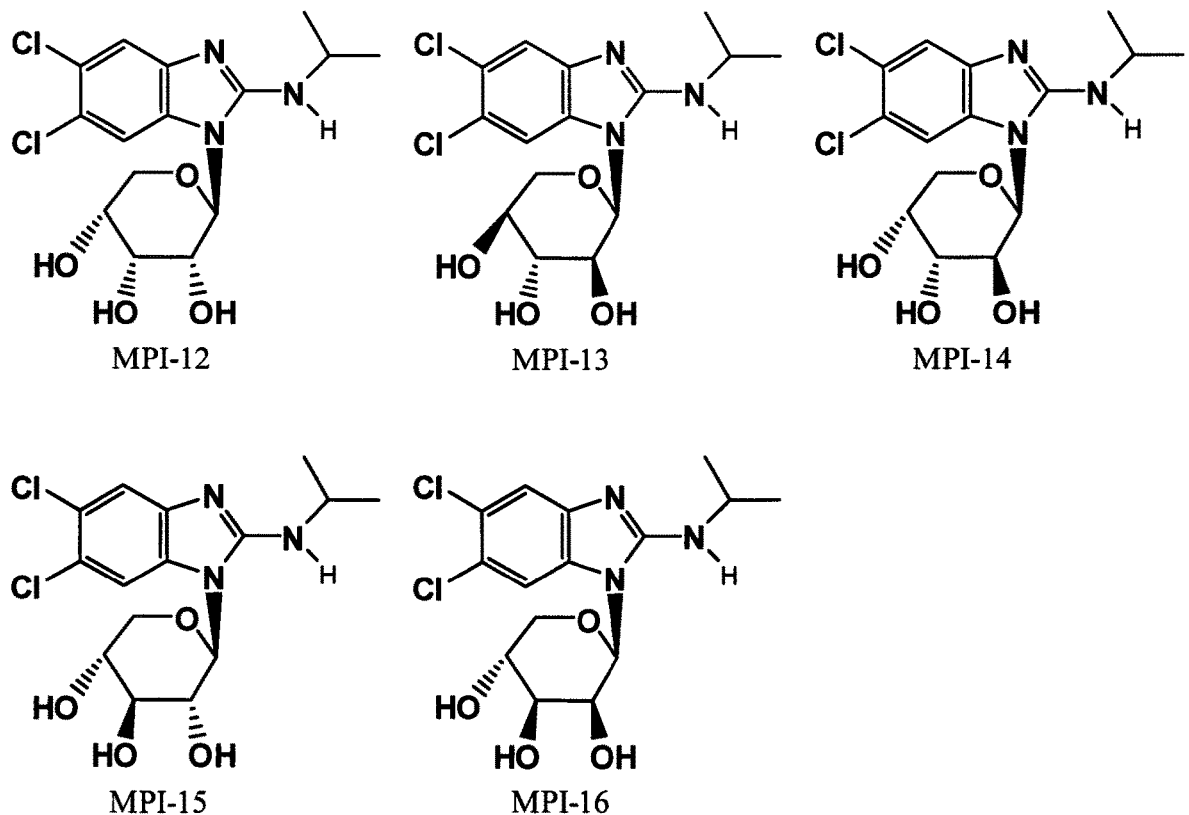

A number of patent and non-patent documents are cited in the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims. Furthermore, the transitional terms "comprising", "consisting essentially of" and "consisting of" define the scope of the appended claims, in original and amended form, with respect to what unrecited additional claim elements or steps, if any, are excluded from the scope of the claims. The term "comprising" is intended to be inclusive or open-ended and does not exclude additional, unrecited elements, methods step or materials. The phrase "consisting of" excludes any element, step or material other than those specified in the claim, and, in the latter instance, impurities ordinarily associated with the specified materials. The phrase "consisting essentially of" limits the scope of a claim to the specified elements, steps or materials and those that do not materially affect the basic and novel characteristic(s) of the claimed invention. All compositions or formulations identified herein can, in alternate embodiments, be more specifically defined by any of the transitional phases "comprising", "consisting essentially of" and "consisting of".

What is claimed is:

1. A composition comprising maribavir and at least one of an antacid which is effective for neutralizing acid that catalyzes isomerization of maribavir, (ii) an antibiotic having activity against a microorganism that mediates isomerization of maribavir, or (iii) an antagonist that inhibits metabolism that induces isomerization of maribavir, said isomerization producing a decrease in the therapeutic efficacy of maribavir.

2. The composition of claim 1, wherein said composition comprises maribavir and an antacid which is effective for neutralizing acid that catalyzes isomerization of maribavir.

3. The composition of claim 1, wherein said composition comprises maribavir and an antibiotic having activity against a microorganism that mediates isomerization of maribavir.

4. The composition of claim 1, wherein said composition comprises maribavir and an antagonist that inhibits metabolism that induces isomerization of maribavir, said isomerization producing a decrease in the therapeutic efficacy of maribavir.

5. The composition of claim 1, wherein said composition comprises at least 100 mg of maribavir.

6. The composition of claim 5, wherein said composition comprises up to 3200 mg of maribavir.

7. The composition of claim 1, wherein said composition is an immediate release formulation, a delayed release formulation, a controlled release formulation or an intravenous formulation.

8. The composition of claim 1, wherein said composition is formulated for oral administration.

9. The composition of claim 1, wherein said composition is formulated for intravenous administration.

* * * * *